(12) United States Patent
Agon

(10) Patent No.: US 12,201,662 B2
(45) Date of Patent: Jan. 21, 2025

(54) **COMPOSITIONS AND METHODS FOR TREATING COVID-19 INFECTIONS WITH AN EXTRACT OF *DICHROSTACHYS GLOMERATA***

(71) Applicant: APIQuest USA, Inc., Washiington, DC (US)

(72) Inventor: Achidi Valentin Agon, Houeyiho (BJ)

( * ) Notice: Subject to any disclaimer, the term of this patent is extended or adjusted under 35 U.S.C. 154(b) by 169 days.

(21) Appl. No.: 17/332,778

(22) Filed: May 27, 2021

(65) Prior Publication Data

US 2021/0369801 A1    Dec. 2, 2021

Related U.S. Application Data

(60) Provisional application No. 62/704,756, filed on May 27, 2020.

(51) Int. Cl.
*A61K 36/48* (2006.01)
*A23L 33/00* (2016.01)
*A23L 33/105* (2016.01)
*A61K 9/00* (2006.01)

(52) U.S. Cl.
CPC ............ *A61K 36/48* (2013.01); *A23L 33/105* (2016.08); *A23L 33/40* (2016.08); *A61K 9/0056* (2013.01); *A23V 2002/00* (2013.01)

(58) Field of Classification Search
None
See application file for complete search history.

(56) References Cited

U.S. PATENT DOCUMENTS

| 3,089,817 A | 5/1963 | Roth et al. |
| 2004/0171674 A1 * | 9/2004 | Rao ............... C07D 311/64 549/406 |
| 2012/0301561 A1 | 11/2012 | Oben |
| 2018/0035705 A1 | 2/2018 | Alter |
| 2023/0076818 A1 | 3/2023 | Agon et al. |

FOREIGN PATENT DOCUMENTS

| WO | WO 2004/052384 | * | 6/2004 |
| WO | WO 2021/224660 | | 11/2021 |

OTHER PUBLICATIONS

El-Sharawy R. et al. Antiviral and Antiparasitic Activities of Clovamide . . . J of Applied Pharmaceutical Science 7(9)219-223, Sep. 2017. (Year: 2017).*

Nkeck, J.R. et al. An alert on the incausious use of herbal medicines by sub-Saharan African populations to fight against the COVID-19, The Pan African Medical Journal, 2020;35 (Supp 2):26.

* cited by examiner

*Primary Examiner* — Terry A McKelvey
*Assistant Examiner* — Catheryne Chen
(74) *Attorney, Agent, or Firm* — FisherBroyles, LLP

(57) ABSTRACT

The present disclosure relates to compositions and methods for treating a subject having a COVID-19 infection. The present disclosure relates to the use of *Dichrostachys glomerata* extract as a medicament for the treatment of COVID-19 infections.

19 Claims, No Drawings

COMPOSITIONS AND METHODS FOR TREATING COVID-19 INFECTIONS WITH AN EXTRACT OF *DICHROSTACHYS GLOMERATA*

FIELD

The present disclosure relates to compositions and methods for treating a subject having a COVID-19 infection. The present disclosure relates to the use of *Dichrostachys glomerata* extract as a medicament for the treatment of COVID-19 infections.

DETAILED DESCRIPTION OF THE DISCLOSURE

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the disclosed compounds or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

As used herein, the term "Coronaviridae" refers to a family of enveloped, positive-sense, single-stranded RNA viruses. The term "coronavirus" refers in the methods described herein specifically to SARS-CoV-2, which causes COVID-19, and which originated in Wuhan China in 2019. The term coronavirus and variations thereof are used interchangeably throughout the disclosure. Other Coronaviridae viruses are used as examples, targets and standards by which the presently disclosed compounds are measured. For example, MERS (Middle East Respiratory Syndrome) coronavirus.

As used herein, the term "subject" refers to a human or an animal that has been diagnosed with COVID-19 or one or more strains of SARS-CoV-2, or has tested positive for COVID-19 or one or more strains of SARS-CoV-2. The term subject also includes humans or animals that have been exposed to Wuhan coronavirus but are not symptomatic.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant for a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient, to minimize any adverse side effects in the subject, and to optimize formulation for drug delivery and dosing to the target tissues infected by Coronaviridae as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

"Test agents" or otherwise "test compounds" as used herein refers to an agent or compound that is to be screened in one or more of the assays described herein. Test agents include compounds of a variety of general types including, but not limited to, small organic molecules, known pharmaceuticals, polypeptides; carbohydrates such as oligosaccharides and polysaccharides; polynucleotides; lipids or phospholipids; fatty acids; steroids; or amino acid analogs. Test agents can be obtained from libraries, such as natural product libraries and combinatorial libraries. In addition, methods of automating assays are known that permit screening of several thousands of compounds in a short period.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

DETAILED DESCRIPTION

*Dichrostachys glomerata* (DG) is a semi-deciduous to deciduous tree up to 7 meters tall with an open crown. Bark on young branches appear green and hairy but dark grey-brown and longitudinally fissured on older branches and stems; smooth on spines formed from modified side shoots. *Dichrostachys glomerata* is a spice commonly used in the Cameroonian cuisine and is also used in traditional Cameroonian medicine as natural remedy for many illness.

The effects of *Dichrostachys glomerata* spice on humans has been studied for many years. For example, Kuate et al., "Effects of *Dichrostachys glomerata* spice of cardiovascular diseases risk factors in normoglycemic and type 2 diabetic obese volunteers," *Food Research International*, Vol. 44, Issue 4, pp. 1197-1202 (2011) reported the potential antioxidant and hypoglycemic properties of the spice and that it is well tolerated in humans. In another study, (Kuate et al., "Anti-inflammatory, anthropometric and lipomodulatory effects Dyglomera® (aqueous extract of *Dichrostachys glomerata*) in obese patients with metabolic syndrome," Functional Foods in Health and Disease 2013; 3(11):416-427) the author concluded: "Dyglomera® reduces the weight and improves the atherogenic risk factors associated with MetS after 8 weeks of treatment. The effects in the current study, which focused on the extract of DG (Dyglomera®), appears to be stronger than those observed in previous studies using whole, ground DG, thus conferring a superior anti-atherogenic capacity on Dyglomera®."

The term "comestible agent" as used herein relates to any vehicle capable of delivering the disclosed *Dichrostachys glomerata* orally. The most common comestible agent is a food or food product whether raw, cooked or processed.

It has now been surprisingly found that the spice derived from *Dichrostachys glomerata* is effective as a cure for COVID-19.

Compositions

One aspect of the disclosure relates to pharmaceutical compositions for use in treating a subject infected with a COVID-19 coronavirus, the pharmaceutical compositions comprising an effective amount of an extract of the plant *Dichrostachys glomerata*.

In one embodiment the composition comprises from about 200 mg to about 1000 mg of an extract of the plant *Dichrostachys glomerata*.

In one iteration the composition comprises the seed of *Dichrostachys glomerata*.

In another iteration the composition comprises the bark of *Dichrostachys glomerata*.

In a further iteration the composition comprises the macerated whole plant *Dichrostachys glomerata*.

In a yet further iteration the composition comprises the pods of *Dichrostachys glomerata*.

In a still yet further iteration the composition comprises the dried pods of *Dichrostachys glomerata* that have been ground into a powder.

The disclosed *Dichrostachys glomerata* extracts can be consumed directly by the subject being treated.

A further aspect of the disclosed pharmaceutical compositions, comprises:
a) an effective amount of an extract of the plant *Dichrostachys glomerata*; and
b) a pharmaceutically acceptable carrier.

Another aspect of the disclosed pharmaceutical compositions, comprises:
a) an effective amount of an extract of the plant *Dichrostachys glomerata*; and
b) one or more adjunct ingredients; and
c) a pharmaceutically acceptable excipient.

In one iteration, the adjunct ingredients are chosen from tannins, flavonoids, saponins, terpenes and steroids.

The extraction can be done using water of pharmaceutically acceptable solvents after which the liquids are removed by evaporation or lyophilization. The dried powder can be further processed into a capsule, pill or suppository. The extraction is further described herein below.

The disclosed compositions comprise an extract of the plant *Dichrostachys glomerata* in an amount from about 200 mg to about 1000 mg. In one embodiment the compositions comprise from about 250 mg to about 750 mg of an extract of the plant *Dichrostachys glomerata*. In another dose embodiment the compositions comprise from about 400 mg to about 600 mg of an extract of the plant *Dichrostachys glomerata*. In a further dose embodiment the compositions comprise from about 250 mg to about 500 mg of an extract of the plant *Dichrostachys glomerata*. In a still further dose embodiment the compositions comprise from about 350 mg to about 800 mg of an extract of the plant *Dichrostachys glomerata*. In a yet further dose embodiment the compositions comprise from about 250 mg to about 350 mg of an extract of the plant *Dichrostachys glomerata*.

The disclosed compositions can provide a single dose of an extract of the plant *Dichrostachys glomerata* based upon the body mass of the subject being treated. Therefore, a single dose of a an extract of the plant *Dichrostachys glomerata* can range from about 0.5 mg/kg to about 20 mg/kg of the subject's body mass. In one embodiment, the amount of an extract of the plant *Dichrostachys glomerata* in a single dose is from about 1 mg/kg to about 8 mg/kg of the subject's body mass. In another embodiment, the amount of an extract of the plant *Dichrostachys glomerata* in a single dose is from about 2 mg/kg to about 5 mg/kg of the subject's body mass. In a further embodiment, the amount of an extract of the plant *Dichrostachys glomerata* in a single dose is from about 1.5 mg/kg to about 4 mg/kg of the subject's body mass. In a yet further embodiment, the amount of an extract of the plant *Dichrostachys glomerata* in a single dose is from about 4 mg/kg to about 10 mg/kg of the subject's body mass. In a still further embodiment, the amount of an extract of the plant *Dichrostachys glomerata* in a single dose is from about 5 mg/kg to about 8 mg/kg of the subject's body mass. For example, the dose can comprise any amount from about 0.5 mg/kg to about 10 mg/kg on the body mass of the subject being treated. For example, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, or 50 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 90 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or 10.0 mg/kg of a subject's body mass.

In one embodiment, symptomatic patients are given 3 capsule each of 350 m every 2 hours 4 to 6 times a day for the first three days of treatment and 3 capsules every 6 hours until obtaining a negative PCR test, typically between 7 and 14 days. In a further embodiment, severe cases are administered 3 capsules of 350 mg every 2 hours for 4 to 7 days to quickly neutralize the Covid-19 virus. If the PCR test is negative after 72 hours of treatment, the patient is instructed to maintain regular hydration. In a further embodiment, adult asymptomatic cases are administered 3 capsules of 350 mg 4 times a day or 3 capsules every 6 hours until the PCR test results are negative. In a yet further embodiment, for adult prophylaxis one capsule of 350 mg is administered daily for the duration of exposure to Covid-19. If during the prophylaxis treatment period the subject becomes symptomatic, the treatment will vary depending upon the evaluation of the subject by medical personnel.

Comestible Agent

The disclosed *Dichrostachys glomerata* extract compositions can comprise a comestible agent, for example, any edible vehicle. The most common disclosed edible vehicle is food. Comestible agents can include any solid food product. Non-limiting examples of comestible agents include meats, fish, fruits, vegetables, dairy products, legumes, pastas, breads, grains, seeds, nuts, spices, and herbs. In addition, the bioavailability enhancing agent and the antiviral agent can be combined into a beverage. Non-limiting examples of beverages includes coffee, tea, milk products and the like.

In one embodiment, the *Dichrostachys glomerata* extracts can be admixed with a food prior to the subject eating the food. For example, admixed with a vegetable, i.e., potatoes, cereals, i.e., porridge and the like.

Carriers

Acceptable carriers or diluents are well known in the art, and are described, for example, in the incorporated material of Remington: The Science and Practice of Pharmacy (20.sup.th ed, Lippincott Williams & Wilkens Publishers (2003)), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The pharmaceutical compositions can additionally include preservatives, solubilizers, stabilizers, wetting agents, emulsifiers, sweeteners, colorants, flavorings, buffers, coating agents, or antioxidants.

Adjunct Ingredients

The following are non-limiting examples of adjunct ingredients suitable for use in the disclosed compositions.

Bile Salts

The disclosed compositions comprise one or more bile salts. The bile salts enhance the ability of the disclosed compositions to target the duodenum. Non-limiting examples of bile salts and/or bile acids includes steroid acids (and/or the carboxylate anion thereof) and salts thereof, found in the bile of an animal (e.g., a human), including cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, lithocolate, and the like. Taurocholic acid and/or taurocholate are referred to herein as TCA.

Bile salts are typically conjugated with glycine or taurine. For example, the term "bile acid" as used herein includes cholic acid conjugated with either glycine or taurine: glycocholate and taurocholate, respectively (and salts thereof). Any reference to a bile salt or bile acid used herein includes reference to an identical compound naturally or synthetically prepared.

Saponins

The process for preparing the disclosed nanoemulsions uses emulsifiers and surfactants to obtain the desired properties. In one aspect the disclosed process utilizes saponins for their emulsification properties.

The disclosed saponins are obtained from naturally occurring sources, for example, the genus *Saponaria*, of the family Caryophyllaceae; *Sapindus* of the family Sapindaceae; in the families Sapindaceae, Hippocastanaceae, *Gynostemma* (*G. pentaphyllum* sp.), and Cucurbitaceae. In addition, saponins can be derived from the genus *Panax*, for example, *Panax quinquefolius, Panax vietnamensis*, and *Panax pseudoginseng*. One non-limiting example of a suitable saponin is "soap bark" obtained from *Quillaja saponaria*, herein referred to as "quillaja."

Terpenes

Non-limiting examples of terpenes suitable for use in the disclosed compositions include geraniol, citronellol, geranial, citronellal, linalool, menthone, rose oxide, alpha-terpineo, α-bisabolol, α-bedrene, α-phellandrene, β-pinene, borneol, camphene, itral, Citronellol, D-limonene, dugenol, beraniol, linalool, menthol, nerol, and phytol.

Tannins

Non-limiting examples of tannins are tannins derived from gallic acid, phloroglucinol, and flavonoids, as well as, the pseudo tannins.

In addition, the disclosed compositions can comprise one or more plant sterols, chalcones, flavonoids, isoflavonoids, and neoflavonoids.

Methods of Use

Disclosed herein are methods for treating a Coronavirus, especially COVID-19.

The disclosed methods comprise administering to a subject in need of treatment an effective amount of a composition comprising an extract of the plant *Dichrostachys glomerata*. In one aspect, the methods comprise administering from about 400 mg to about 600 mg of a disclosed composition at least once a day. In one iteration, the subject is administered the composition twice a day. In another iteration, the subject is administered the composition three times a day.

The disclosed compositions were administered to human subjects. The amount given was 500 mg every six hours for a minimum of 7 days. Table I provides the results of the treatments.

In the above examples the composition can be administered via comestible agent or in a pharmaceutical delivery system, for example, a capsule.

TABLE I

| Patient age | sex | COVID-19 diagnosis* | End of symptoms | Negative test for COVID-19 | End treatment |
|---|---|---|---|---|---|
| 58 | M | 11 Mar. | 20 Mar. | 25-Mar. | 28-Mar. |
| 62 | F | 11 Mar. | 13 Mar. | 19-Mar. | 23-Mar. |
| 27 | M | 16 Mar. | 20 Mar. | 29-Mar. | 19-Mar. |
| 25 | F | 16 Mar. | 20 Mar. | 29-Mar. | 19-Mar. |
| 19 | F | 16 Mar. | 20 Mar. | 29-Mar. | 19-Mar. |
| 6 | F | 16 Mar. | — | 29-Mar. | 19-Mar. |
| 48 | F | 31 Mar. | — | 10-Apr. | 10-Apr. |
| 20 | F | 30 Mar. | — | 10-Apr. | 10-Apr. |
| 58 | M | 11 Mar. | 20 Mar. | 25-Mar. | 28-Mar. |
| 62 | F | 11 Mar. | 13 Mar. | 19-Mar. | 23-Mar. |
| 27 | M | 16 Mar. | 20 Mar. | 29-Mar. | 19-Mar. |
| 25 | F | 16 Mar. | 20 Mar. | 29-Mar. | 19-Mar. |
| 19 | F | 16 Mar. | 20 Mar. | 29-Mar. | 19-Mar. |
| 6 | F | 16 Mar. | — | 29-Mar. | 19-Mar. |
| 58 | M | 23 Mar. | 30 Mar. | 4-Apr. | 4-Apr. |
| 62 | M | 9 Apr. | 12 Apr. | 14-Apr. | 14-Apr. |

*All dates are 2020.

As can be seen in the results of Table I, the disclosed compositions and methods are effective in treating COVID-19 infections in humans.

Method of Extraction

The Weighing of the Harvested Plant

The total quantity to be extracted must be weighed and noted. This step is very important because the quality of the principle active ingredients depends on the total weight of the macerated plant. During the weighing the branches larger than two centimeters must be removed, otherwise they influence the total weight and distort the weight ratio to the quality of the active ingredient.

Extraction

The first step is to submerge the leaves under water and bring the vessel to a boil for 45 minutes after which the water lost to evaporation is replaced. Boiling is continued for 90 minutes, which includes replacement of lost water. The heat is removed and the leaves are left to steep in the extraction water for 6 hours. The same extraction water can be readily used for subsequent extractions because there would be a higher concentration of actives and therefore less water to remove to obtain the desired material.

The leaves are removed, rinsed, and the rinsing water combined with the extraction solution from above. The extraction step is repeated and the leaves thoroughly rinsed. The combined rinse and extraction solutions are evaporated to dryness. This yields a black substance having a pH of from about 3 to about 4. Towards the end of evaporation care is taken not to char the isolated ingredients.

According to this procedure, 100 kg of macerated plant leaves can yield 3100 gm of the desired extract. A commercialized preparation is sold under the tradename Aprivirine™.

The isolated extract can be package as capsules or admixed with a solid carrier and pressed into pill form. The amount of excipient is adjusted to deliver the therapeutically effective amount of *Dichrostachys glomerata* extract.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for treating a subject infected with COVID-19, comprising administering to the subject an effective amount of an extract of the plant *Dichrostachys glomerata*.

2. The method according to claim 1, wherein the subject in need is administered composition comprising:
   a) the effective amount of the extract of the plant *Dichrostachys glomerata*; and
   b) one or more carriers or adjunct ingredients.

3. The method according to claim 2, wherein the composition further comprises at least one adjunct ingredient selected from the group consisting of bile salts, saponins, emulsifiers, terpenes, tannins, or plant sterols.

4. The method according to claim 2, wherein the composition further comprises at least one adjunct ingredient selected from the group consisting of preservatives, solubilizers, stabilizers, wetting agents, emulsifiers, sweeteners, colorants, flavorings, buffers, coating agents, or antioxidants.

5. The method according to claim 1, wherein the effective amount comprises about 200 mg to about 1000 mg of the extract of *Dichrostachys glomerata*.

6. The method according to claim 1, wherein the effective amount comprises about 250 mg to about 750 mg of the extract of *Dichrostachys glomerata*.

7. The method according to claim 1, wherein the effective amount comprises about 400 mg to about 600 mg of the extract of *Dichrostachys glomerata*.

8. The method according to claim 1, wherein the effective amount comprises about 250 mg to about 600 mg of the extract of *Dichrostachys glomerata*.

9. The method according to claim 1, wherein the effective amount comprises about 350 mg to about 800 mg of the extract of *Dichrostachys glomerata*.

10. The method according to claim 1, wherein the effective amount comprises about 250 mg to about 350 mg of the extract of *Dichrostachys glomerata*.

11. The method according to claim 1, wherein the effective amount comprises about 350 mg of the extract of *Dichrostachys glomerata*.

12. The method according to claim 2, wherein a single dose of the of comprises an amount of the extract of the plant *Dichrostachys glomerata* of about 0.5 mg/kg to about 20 mg/kg of the subject's body mass.

13. The method according to claim 1, wherein the extract is administered in the form of a capsule.

14. The method according to claim 1, wherein the extract is administered combined with a comestible agent.

15. The method according to claim 14, wherein the comestible agent is food.

16. A method for treating a subject symptomatic with Covid-19 infection, comprising administering to the subject a medicament comprising about 200 mg to about 500 mg of an extract of the plant *Dichrostachys glomerata* about 2 to about 5 times a day every 3 to 6 hours daily until the subject tests negatively for Covid-19.

17. A method for treating a subject exhibiting a severe case of Covid-19 infection, comprising administering to the subject a medicament comprising about 300 mg to about 500 mg of an extract of the plant *Dichrostachys glomerata* about 3 to about 5 times a day every 4 to 6 hours daily until the subject tests negatively or other for Covid-19.

18. A method for treating a subject asymptomatic with Covid-19 infection, comprising administering to the subject a medicament comprising about 200 mg to about 500 mg of an extract of the plant *Dichrostachys glomerata* about 2 to about 5 times a day every 3 to 6 hours daily until the subject tests negatively for Covid-19.

19. A method for treating a subject prophylactically wherein the subject has been exposed to Covid-19 infection, comprising administering to the subject a medicament comprising about 300 mg to about 400 mg of an extract of the plant *Dichrostachys glomerata* during the duration of exposure to Covid-19.

* * * * *